(12) United States Patent
Predham et al.

(10) Patent No.: US 10,799,112 B2
(45) Date of Patent: Oct. 13, 2020

(54) TECHNIQUES FOR PROVIDING COMPUTER ASSISTED EYE EXAMINATIONS

(71) Applicant: SIMPLE CONTACTS, INC., New York, NY (US)

(72) Inventors: Joseph Predham, Brooklyn, NY (US); David Quigley, Greenport, NY (US); Nicholas Ficano, Astoria, NY (US); Joel Wishkovsky, Brooklyn, NY (US)

(73) Assignee: SIMPLE CONTACT, INC., New York, NY (US)

( * ) Notice: Subject to any disclaimer, the term of this patent is extended or adjusted under 35 U.S.C. 154(b) by 91 days.

(21) Appl. No.: 15/966,944

(22) Filed: Apr. 30, 2018

(65) Prior Publication Data

US 2018/0317766 A1  Nov. 8, 2018

Related U.S. Application Data

(60) Provisional application No. 62/500,089, filed on May 2, 2017.

(51) Int. Cl.
*A61B 3/10* (2006.01)
*A61B 3/11* (2006.01)
(Continued)

(52) U.S. Cl.
CPC ............ *A61B 3/111* (2013.01); *A61B 3/0025* (2013.01); *A61B 3/0041* (2013.01);
(Continued)

(58) Field of Classification Search
CPC ........ A61B 3/111; A61B 3/0025; A61B 3/11; A61B 3/113; A61B 3/1216; A61B 3/0008;
(Continued)

(56) References Cited

U.S. PATENT DOCUMENTS

| | | | |
|---|---|---|---|
| 6,238,049 B1 * | 5/2001 | Griffin | A61B 3/028 351/243 |
| 2011/0129143 A1 * | 6/2011 | Keating | H04N 13/261 382/154 |

(Continued)

OTHER PUBLICATIONS

PCT International Search Report and Written Opinion dated Aug. 16, 2018 for PCT International Application No. PCT/US2018/030410, 11 pages.

(Continued)

*Primary Examiner* — Brandi N Thomas
(74) *Attorney, Agent, or Firm* — RMCK Law Group, PLC

(57) ABSTRACT

A computer-readable medium includes computer-executable instructions that cause a processing unit of a user device to instruct a user to stand a predetermined distance from the user device, acquire an image of the user, and determine a user interpupillary distance based on the acquired image. The user interpupillary distance indicates a distance between the user's pupils in terms of pixels. The computer-executable instructions further cause the processing unit to determine a current distance between the user and the user device based on the user interpupillary distance, a predetermined interpupillary distance, a width of the acquired image in terms of pixels, and a field of view of the camera. Additionally, the computer-executable instructions cause the processing unit to display the current distance between the user and the user device on a display and display an eye chart when the determined current distance is equal to the predetermined distance.

22 Claims, 14 Drawing Sheets

(51) Int. Cl.
*A61B 3/00* (2006.01)
*A61B 3/14* (2006.01)
*A61B 3/032* (2006.01)
*G16H 40/60* (2018.01)
*G16H 30/40* (2018.01)

(52) U.S. Cl.
CPC ............ *A61B 3/0058* (2013.01); *A61B 3/032* (2013.01); *A61B 3/145* (2013.01); *G16H 30/40* (2018.01); *G16H 40/60* (2018.01)

(58) Field of Classification Search
CPC ..... A61B 3/0041; A61B 3/0058; A61B 3/032; A61B 3/085; A61B 3/112; A61B 3/145; A61B 3/152
USPC ........ 351/200, 204–206, 209–211, 221, 222, 351/243–246
See application file for complete search history.

(56) References Cited

U.S. PATENT DOCUMENTS

| | | | |
|---|---|---|---|
| 2014/0152956 A1* | 6/2014 | Silva | A61B 3/111 351/204 |
| 2014/0375954 A1 | 12/2014 | Berry et al. | |
| 2015/0190048 A1* | 7/2015 | Huang | A61B 3/024 351/239 |
| 2016/0353987 A1 | 12/2016 | Carrafa et al. | |
| 2017/0112373 A1 | 4/2017 | Burns et al. | |
| 2017/0202450 A1* | 7/2017 | Carrafa | A61B 3/0033 |

OTHER PUBLICATIONS

U.S. Appl. No. 62/245,811, filed Oct. 23, 2015, entitled "Photorefraction Method and Product," 49 pages.
U.S. Appl. No. 62/245,820, filed Oct. 23, 2015, entitled "Visual Acuity Testing Method and Product," 64 pages.
Constine, J., "Opternative's Online Eye Exam Gets You a Glasses Prescription From Home," dated Jul. 27, 2015, https://techcrunch.com/2015/07/27/online-eye-test/, accessed on May 17, 2018, 6 pages.
Dodgson, N., "Variation and extrema of human interpupillary distance," Conference Paper in Proceedings of SPIE—The International Society for Optical Engineering, Jan. 2004, 12 pages.
Simple Contacts, "Hassel-free contact lenses. Prescription renewal without an office visit.," www.simplecontacts.com website dated Apr. 6, 2016, website accessed Jan. 5, 2020 at https://web.archive.org/web/20160406205458/https://www.simplecontacts.com/, 4 pages.

* cited by examiner

Tell us about yourself and we'll check availability in your state

Enter Email Address

State | Age: 22

Last Dilated Eye Exam: July 2015

Skip | Submit

FIG. 5A

Our test takes two minutes. Please ensure:

✓ Wearing contacts

✓ 10ft of space

✓ Well-lit room

Skip | Continue

FIG. 5B

✓ Do you see clearly in your contact lenses?

No | Yes

FIG. 5C

✓ Do you have any pain or discomfort in your contact lenses?

Yes | No

FIG. 5D

✓ Do you understand that this is a vision test only and not a substitute for a dilated eye health exam?

No | Yes

FIG. 5E

Do you have any of the listed health conditions:

Cataracts
Color blindness
Pain in your eyes
Diabetes
Double vision
Eye infection
Recent eye surgery
Flashes or floaters
Glaucoma
Heart disease
Hereditary eye disease
High blood pressure
High cholesterol Yes | No

Cart

1. Take renewal test

Test comlete
✓ Redness Test
✓ Visual Acuity Test
✓ Signed Waiver

2. Select my brand

[Search for my brand]

[Checkout]

FIG. 9B

Search for my brand

🔍 Enter search for lenses

Acuvue Oasys with Hydraclear 12 pack

1-Day Acuvue Moist 90 pack

Air Optix Aqua

Acuvue 2

Acuvue Oasys for Astigmatism

1-Day Acuvue 30 pack

Right Eye (OD)    Left Eye (OS)

Acuvue Oasys with Hydraclear 12 pack | Acuvue Oasys with Hydraclear 12 pack

Change lens | Change lens

BC: None | BC: None
Dia: 14.00 | Dia: 14.00
Power: None | Power: None

[Continue]

TECHNIQUES FOR PROVIDING COMPUTER ASSISTED EYE EXAMINATIONS

CROSS-REFERENCE TO RELATED APPLICATIONS

This application claims the benefit of U.S. Provisional Application No. 62/500,089, filed on May 2, 2017. The disclosure of the above application is incorporated herein by reference in its entirety.

FIELD

The present disclosure relates to providing eye examinations.

BACKGROUND

Physicians can perform a series of eye tests to assess a patient's vision and ability to focus. For example, a physician may test a patient's visual acuity by having the patient read letters from an eye chart posted in the physician's office. The visual acuity test may test the patient's clarity of vision. Poor performance on the visual acuity test may indicate that the patient has one or more eye disorders or diseases. The physician may write a prescription for an underperforming patient, which the patient can use to purchase corrective optics, such as contact lenses and/or glasses.

SUMMARY

In one example, the present disclosure is directed to a non-transitory computer-readable medium comprising computer-executable instructions. The computer-executable instructions cause a processing unit of a user device to instruct a user to stand a predetermined distance away from the user device, acquire an image of the user using a camera, and determine a user interpupillary distance based on the acquired image. The user interpupillary distance indicates a distance between the user's pupils in terms of pixels. The computer-executable instructions further cause the processing unit to determine a current distance between the user and the user device based on the user interpupillary distance, a predetermined interpupillary distance, a width of the acquired image in terms of pixels, and a field of view of the camera. Additionally, the computer-executable instructions cause the processing unit to display the current distance between the user and the user device on a display and display an eye chart on the display when the determined current distance is equal to the predetermined distance.

In another example, the present disclosure is directed to a non-transitory computer-readable medium comprising computer-executable instructions. The computer-executable instructions cause a processing unit of a user device to instruct a user to stand a predetermined distance away from the user device, acquire an image of the user using a camera, and transmit the image to a remote eye test system via a network. The computer-executable instructions further cause the processing unit to receive a user interpupillary distance value from the eye test system via the network. The user interpupillary distance indicates a distance between the user's pupils in terms of pixels. Additionally, the computer-executable instructions cause the processing unit to determine a current distance between the user and the user device based on the user interpupillary distance, a predetermined interpupillary distance, a width of the acquired image in terms of pixels, and a field of view of the camera. The computer-executable instructions further cause the processing unit to display the current distance between the user and the user device on a display and display an eye chart on the display when the determined current distance is equal to the predetermined distance.

BRIEF DESCRIPTION OF THE DRAWINGS

The present disclosure will become more fully understood from the detailed description and the accompanying drawings.

FIGS. 5A-5F illustrate example graphical user interfaces (GUIs) for collecting user information and providing user instructions.

FIGS. 9A-9C illustrate example GUIs for ordering contact lenses.

In the drawings, reference numbers may be reused to identify similar and/or identical elements.

DETAILED DESCRIPTION

Figure 1:
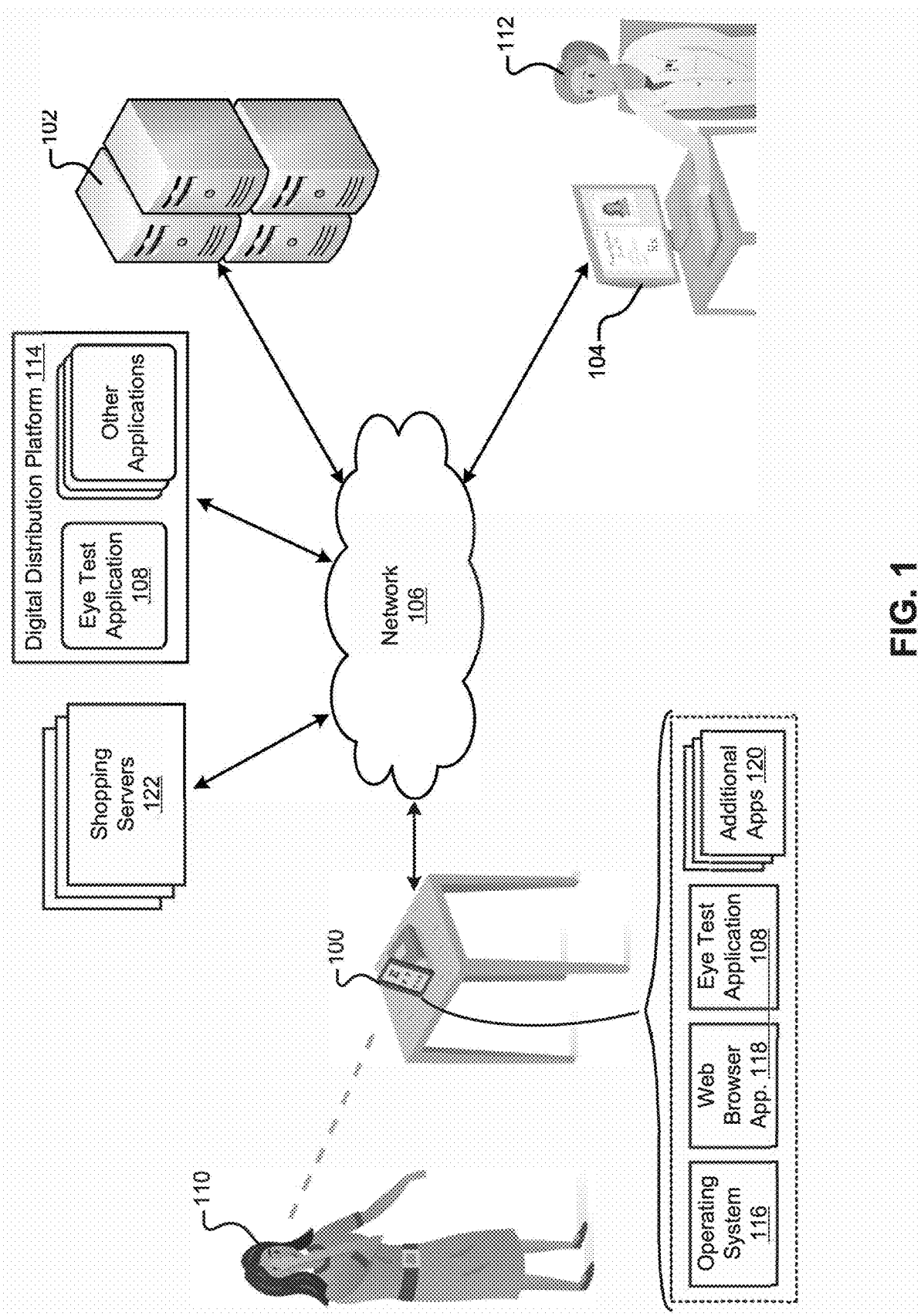
FIG. 1 illustrates an environment that includes a user device that executes an eye test application in communication with an eye test system.

The disclosure is directed to an eye test software application and remote eye test system that assist a user in performing one or more eye tests, such as a red reflex test and/or a visual acuity test. The user may use their computing device (e.g., smartphone, tablet, laptop, or desktop) to run the eye test software application (hereinafter "test application"). In some implementations, while running the test application, the user device may communicate with the remote eye test system (hereinafter "test system") in order to analyze and generate data associated with the one or more eye tests. The test system can provide eye test data associated with the eye tests to a physician for review. Example eye test data may include user information, images, and video recordings. Upon approval of the eye tests, the physician may make a prescription for the user (e.g., a prescription for contact lenses or eye glasses). The user may then order contact lenses and/or eye glasses using the test application.

The test application and test system may provide users with the ability to take eye tests remotely (e.g., at home), without the presence of a physician. For example, a user may download the test application onto their computing device (referred to herein as a "user device"), take the eye tests using the test application, and submit the eye test data to the test system (e.g., a remote server). A physician may then retrieve the eye test data from the test system for review and approval. The user may be notified of the results (e.g., a prescription) via the user device and subsequently order their contact lenses. The remote eye tests may be convenient for both the user and the physician, as the testing and review may be performed at their convenience without an in-person meeting.

Although the test application and test system may be used for convenient remote ordering of contact lenses (e.g., from home), the test application and test system described herein may be used in a variety of different contexts. For example, the test application and test system may be used for vision tests at various locations, including a physician's office, at a Department of Motor Vehicles (DMV) office, or at a kiosk in a pharmacy/store that sells contacts and/or eye glasses. For example, the functionality attributed to the user device and test application herein may be implemented in other computing devices at these locations.

Although a test application installed on a user device may be used to complete the eye tests and submit eye test data, in some implementations, the test system and test application together may provide the functionality to complete the eye tests. For example, some of the functionality attributed to the test application herein may be performed by the test system (e.g., see FIG. 14). In other implementations, the test system may provide a web-based interface that provides similar functionality as the test application. For example, using a web browser application, the user may access a website provided by the test system that provides similar functionality as the test application. In these implementations, the user may refrain from downloading the test application and instead perform the eye tests, submit the eye test data, and order contacts via the provided web-based interface. A web application may be implemented as a set of hypertext markup language (HTML), cascading style sheets (CSS), and Javascript files, along with other assets. These assets may be requested using the hypertext transfer protocol secure (HTTPS) protocol and executed by the web browser application. These assets may be selectively loaded in bundles to reduce latency for the user. In some implementations, the assets may be distributed as a slimmed down set of web files that include the exam experience, which can then be embedded into a partner website where the partner handles checkout and purchase of the contact lenses. In other implementations, the functionality associated with the eye exams can be implemented as embedded software on a computing device equipped with a camera, a microphone, a speaker, and an input source, such as a keyboard. For example, the functionality may be included on a kiosk in a commercial setting, which may be periodically updated with updated software retrieved from the test system 102.

Figure 2:
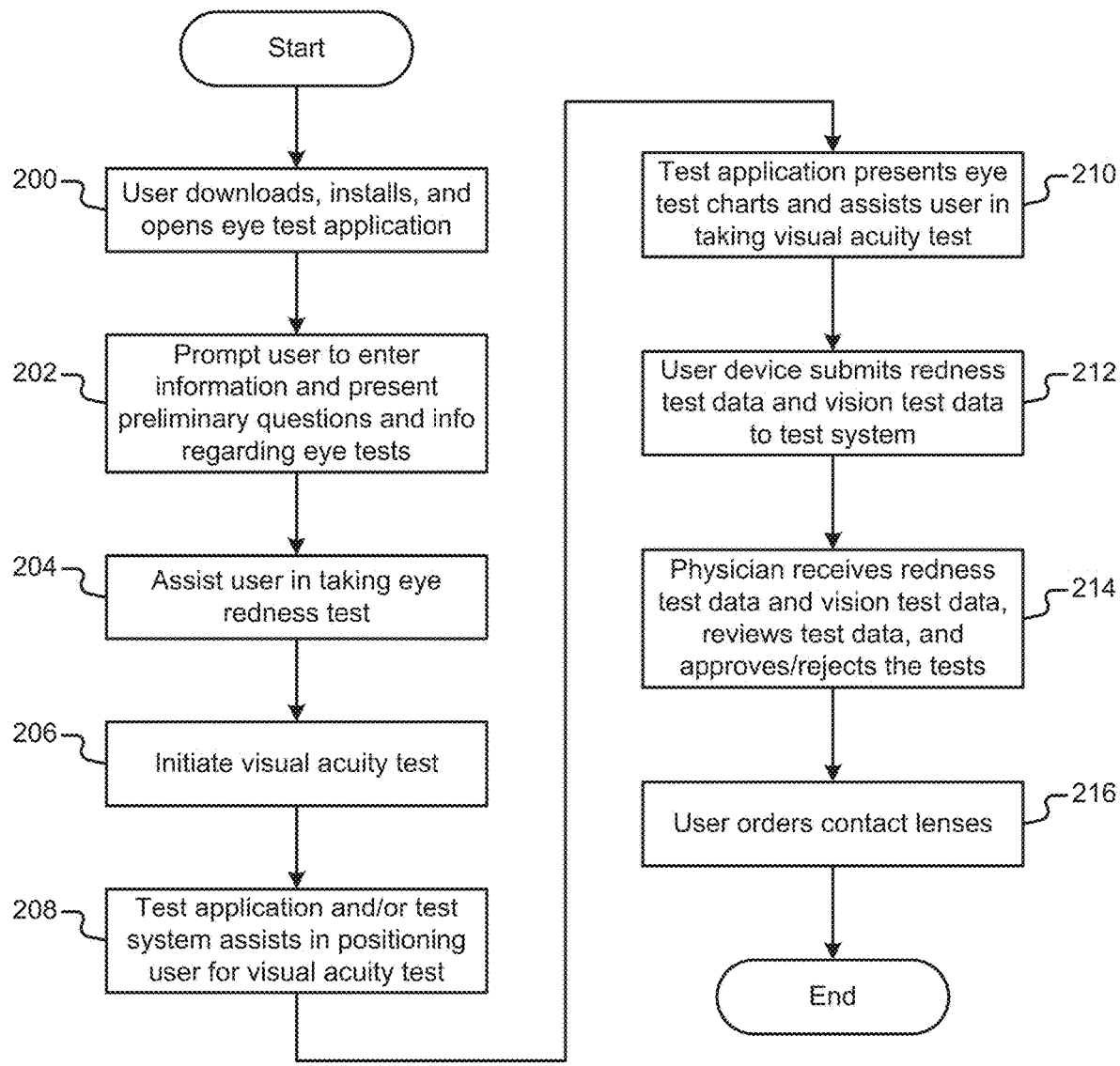
FIG. 2 is a flow diagram of an example method for performing eye examinations using an eye test application and an eye test system.
Figure 11:
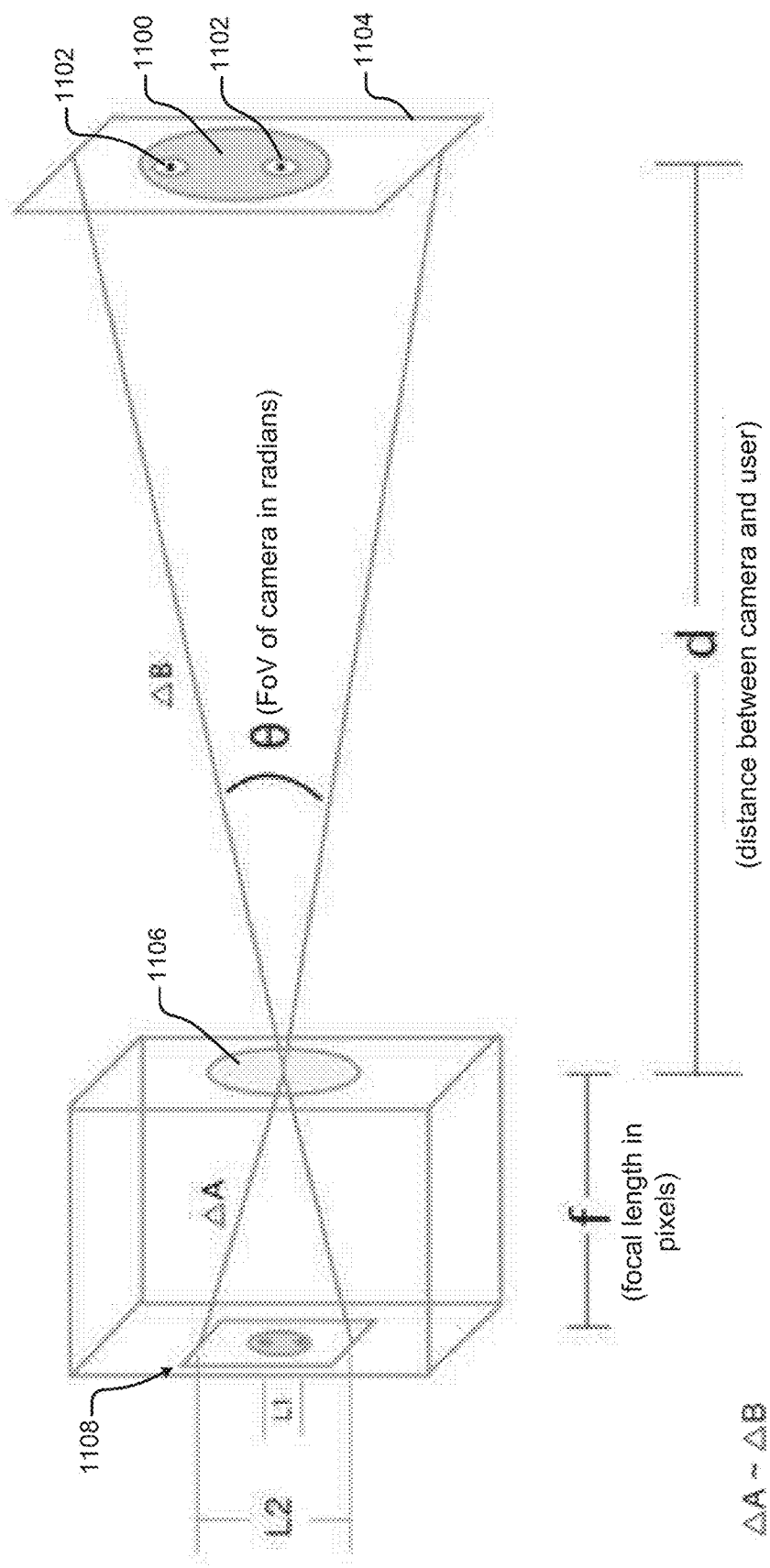
FIG. 11 is a diagram that illustrates calculation of user distance from a user device.
Figure 12:
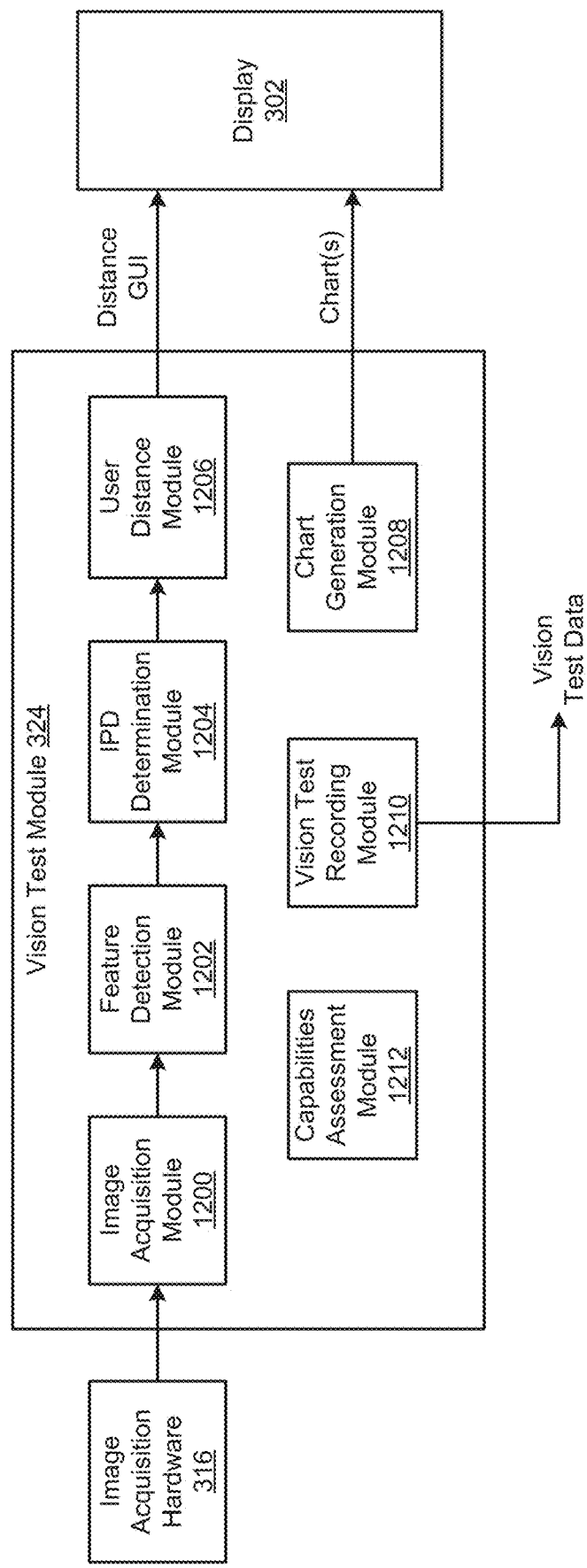
FIG. 12 is a functional block diagram of an example vision test module that assists a user in performing a visual acuity test.
Figure 13:
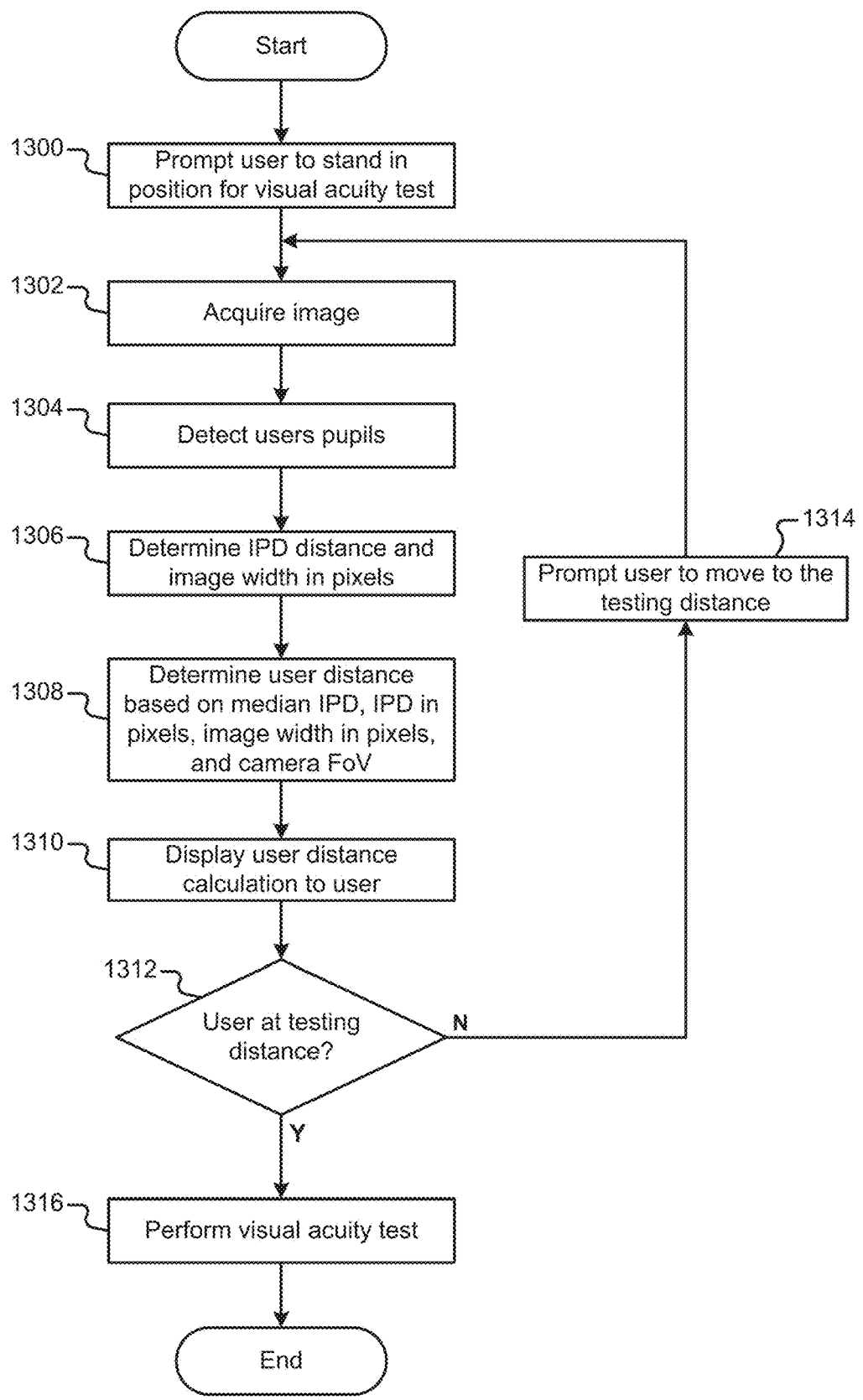
FIG. 13 is a flow diagram of an example method for calculating user distance from a user device.
Figure 14:
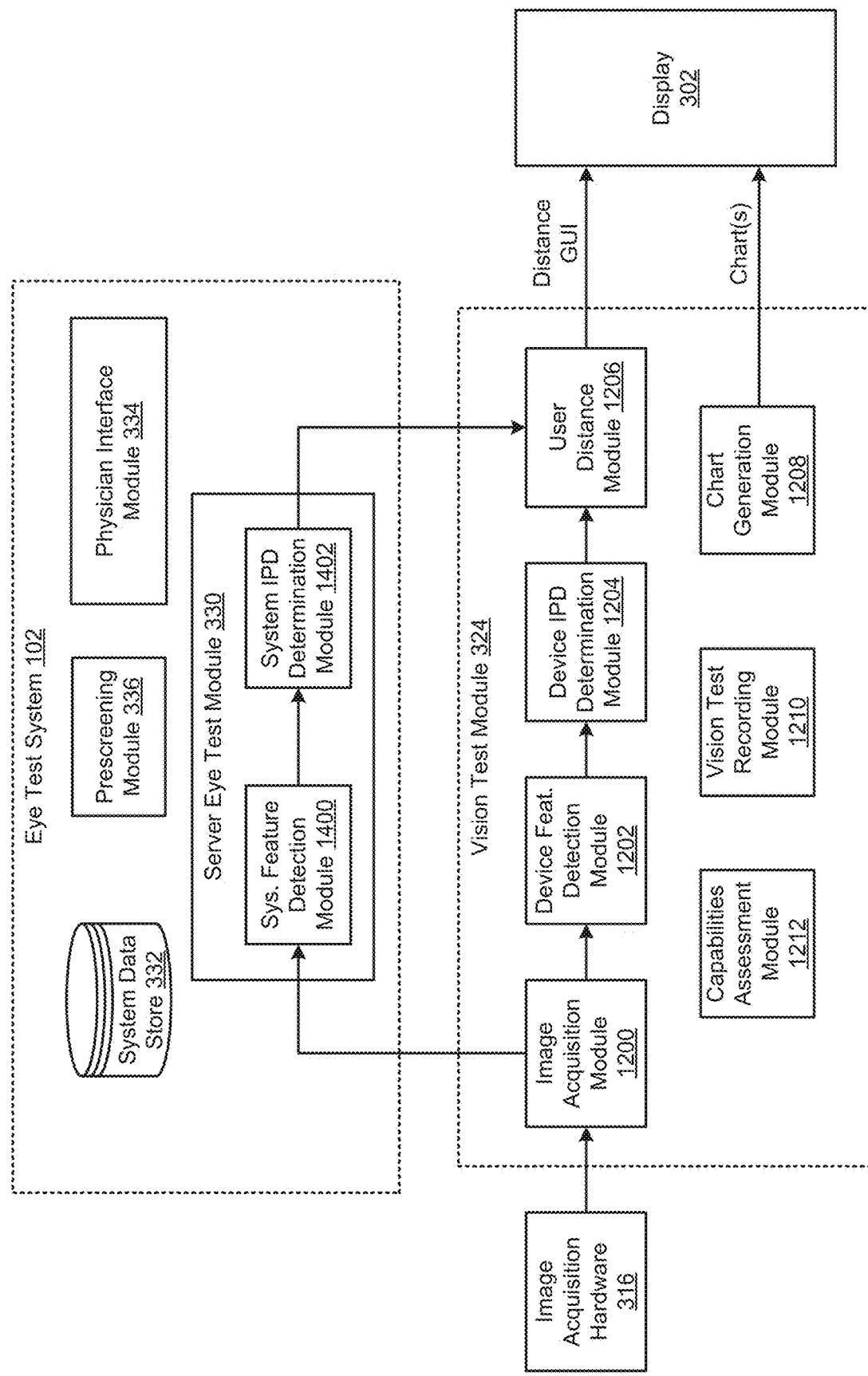
FIG. 14 is a functional block diagram that illustrates an example vision test module and an example test system operating together to assist a user in performing a visual acuity test.

FIGS. 1-14 illustrate techniques for performing eye tests using a test application and/or a remote test system. FIGS. 1-2 are directed to an environment in which a user may download a test application, perform eye tests, and purchase contacts after physician approval of the eye tests. FIGS. 3-10 illustrate detailed examples of the test application and the test system along with example eye test graphical user interfaces (GUIs). FIGS. 11-13 illustrate additional detailed examples directed to determining the distance of a user from the user device during a visual acuity test. FIG. 14 illustrates an example division of functionality between the test application and the test system during the visual acuity test.

FIG. 1 illustrates an environment that includes a user device 100, a test system 102, and a physician device 104 in communication with one another via a network 106. The network 106 may include various types of networks, such as a local area network (LAN), wide area network (WAN), and/or the Internet. The test system 102 and the test application 108 may be provided by a party (e.g., a business) that facilitates remote eye tests for the convenience of the user 110 and physician 112. For example, the party may develop the test application 108, upload the test application 108 to a digital distribution platform 114, and act as the owner/operator of the test system 102. The user 110 may download and install the test application 108 on the user device 100. For example, the user 110 may download the test application 108 from the digital distribution platform 114, such as the GOOGLE PLAY® digital distribution platform by Google, Inc. or the APP STORE® digital distribution platform by Apple, Inc.

The user device 100 executes the test application 108 and communicates with the test system 102 in order to provide the eye test functionality described herein. For example, the user device 100 may communicate with the test system 102 in order to provide an eye test, submit the eye test data to a physician 112, and facilitate the purchasing of contact lenses upon physician approval. Example user devices may include, but are not limited to, a smartphone, tablet computer, laptop computer, or desktop computer. In general, any computing device including a display and a camera (e.g., facing the same direction as the display) can be used for the eye tests. In some cases, multiple devices can be used, such as a separate camera, display (e.g., a monitor), and computing device (e.g., a desktop tower).

The user device 100 can include an operating system 116, one or more web browser applications 118, the installed test application 108, and additional applications 120. Example operating systems may include, but are not limited to, ANDROID® developed by Google Inc., IOS® developed by Apple Inc., MICROSOFT WINDOWS® by Microsoft Corporation, MAC OS® by Apple, Inc., and Linux. Although the test application 108 can be used to provide the eye tests, in some implementations, the test system 102 may provide a web-based interface that is accessible by the web browser application 118. The web-based interface may provide similar functionality as the test application 108.

The environment includes one or more shopping servers 122 that sell contact lenses to users. In some cases, the owner/operator of the test system 102 may own/operate a shopping server 122 that sells contact lenses to the users. The user may also purchase contact lenses from shopping servers 122 that are owned/operated by other parties. In some implementations, the user may use the test application 108 to purchase contact lenses from the shopping servers 122. In other implementations, the user may use the web browser 118 to purchase contact lenses from the shopping servers 122. In some cases, the digital prescription can be used to buy contact lenses in a retail store location.

FIG. 1 illustrates a physician computing device 104 ("hereinafter physician device 104"). The physician device 104 represents a computing device that a physician 112 may use to communicate with the test system 102. The physician 112 may use the physician device 104 to retrieve eye test data from the test system 102, review the eye test data, and provide feedback on the eye tests. Example feedback may include approval of the eye tests or rejection of the eye tests. For example, the physician 112 may reject the eye tests due to failures by the user 110 and/or insufficient test quality, such as bad lighting. In some implementations, the physician device 104 may communicate with the test system 102 using a web-based interface that allows the physician 112 to retrieve eye test data, review the eye tests, and provide feedback. In other implementations, the physician device 104 may include an installed application that is tailored to provide such functionality.

FIG. 2 illustrates an example method that describes how a user and physician may interact with the test system 102 to facilitate remote eye tests. Initially, in block 200, the user downloads, installs, and opens the test application 108 on the user device 100. In block 202, the test application 108 may prompt the user to provide user information (e.g., FIGS. 5A-5F), such as state of residence, age, and last dilated eye exam date. The test application 108 may also present information to the user regarding what to expect during the eye tests and prompt the user to answer questions relevant to the eye tests.

The user can then begin the eye tests. In the example method of FIG. 2, the eye tests include an eye redness test followed by a visual acuity test. In block 204, the test application 108 assists the user in taking the eye redness test. Example GUIs for the eye redness test are illustrated in FIGS. 6A-6D. The physician may use eye redness test data to a) determine how current contact lenses sit on the user's eyes and b) to ensure there are no signs of inflammation.

In block 206, the test application 108 initiates the visual acuity test. With respect to FIG. 7A, the test application 108 may prompt the user to proceed with the visual acuity test by placing the user device 100 in a fixed position (e.g., on a chair, countertop, table, shelf, etc.) and standing a predetermined distance from the user device (referred to herein as the "testing distance"). In block 208, the test application 108 and/or the test system 102 assist the user in finding the correct position for the visual acuity test. For example, the test application 108 and/or the test system 102 may determine the user's distance from the user device 100 and assist the user in positioning themselves at the testing distance from the user device 100. The test application 108 may assist the user in finding the correct position by displaying their current distance from the user device 100 (e.g., FIGS. 7B-7C). As described herein, the test application 108 and/or the test system 102 may determine the distance between the user 110 and the device 100 based on a calculated distance between the user's pupils (i.e., a user's interpupillary distance), an interpupillary distance value (e.g., median value) of a measured population, and other factors described with respect to FIG. 11. The interpupillary distance values may refer to the distance between the centers of an individual's pupils.

Figure 8B:
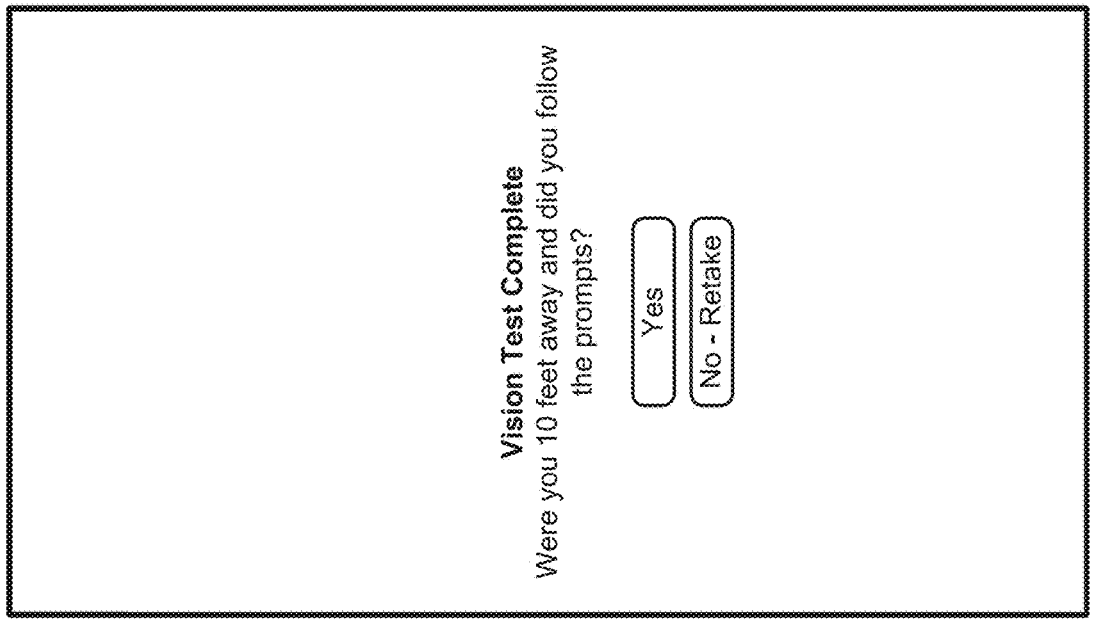
FIGS. 8A-8B illustrate example GUIs used to perform a visual acuity test.
Figure 8A:
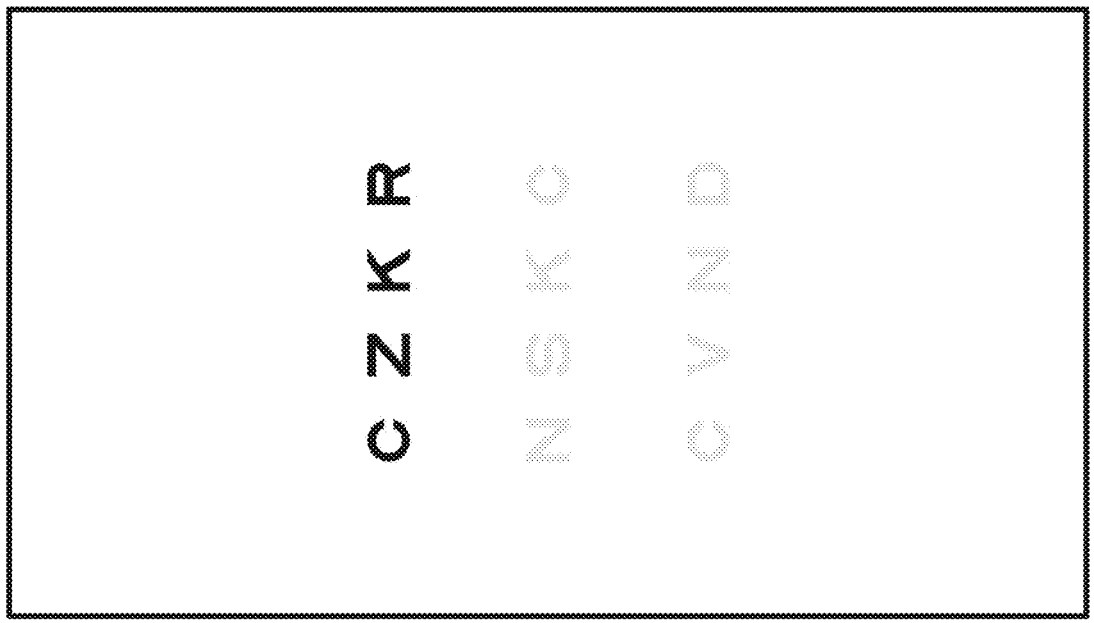

In response to the user 110 positioning themselves at the testing distance, in block 210, the test application 108 may present the user with one or more eye test charts and assist the user in taking the visual acuity test (FIGS. 8A-8B). After completing the visual acuity test, in block 212, the user device 100 may submit the redness test data and the vision test data to the test system 102. In block 214, the physician 112 may receive the redness test data and vision test data, review the test data, and approve or reject the tests. In the case where the physician 112 approves the eye tests, the physician 112 may provide a prescription for contact lenses.

In block 216, the user 110 uses the test application 108, or another application, to order contact lenses based on the prescription. In the case where the physician 112 rejects the tests, the physician (e.g., via the test system 102) may instruct the user 110 to retake the eye tests and/or visit a physician for a full eye-health exam.

Figure 3:
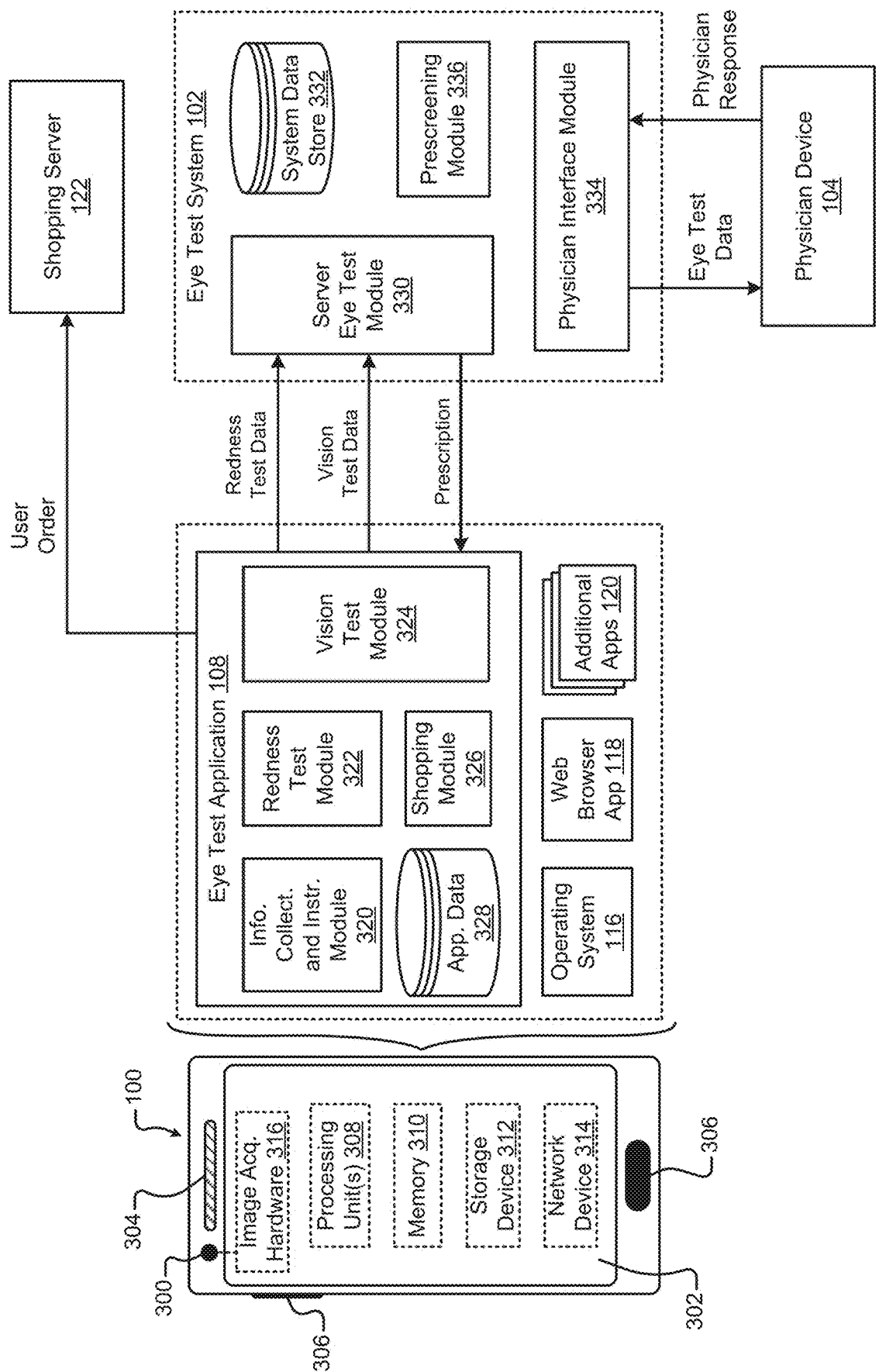
FIG. 3 is a functional block diagram of an example eye test application and an eye test system.

FIG. 3 illustrates an example user device that can execute test application. The device includes a camera 300, a touchscreen display 302, and other user interface devices, such as a speaker 304, a microphone (not illustrated) and input buttons 306. The user device 100 can include electronic hardware that implements the functionalities attributed to the user device 100 herein. For example, the user device 100 can include one or more processing units 308 (i.e., processors), such as central processing units (CPUs) and/or graphics processing units (GPUs). The user device 100 can include memory 310 (e.g., main memory, such as random-access memory), a storage device 312, and a network device 314. The components of the user device 100 may be interconnected by a bus or other communication circuitry. The user device 100 may include additional components that are not illustrated shown in FIG. 3.

The processing unit 308 can execute computer-executable instructions in the memory 310. For example, the processing unit 308 can execute the test application 108, an operating system 116, the web browser application 118, and additional applications 120, all of which can be implemented as computer-executable instructions. The memory 310 and storage device 312 can include one or more computer-readable mediums (e.g., random-access memory, hard disk drives, solid state memory drives, flash memory drives, etc.) that can store any suitable data that is utilized by the operating system 116 and/or any of the applications that are executed by the user device 100. In some implementations, the storage device 312 may include non-volatile memory. The network device 314 may be configured to perform wired and/or wireless communication with the network 106.

The user device includes image acquisition hardware 316 that, with the camera 300, may acquire images and/or video of the user and make the images available to the test application 108. The image acquisition hardware 316 and the camera 300 may include one or more lenses, an image sensor (e.g., a charge-coupled device or complimentary metal-oxide-semiconductor sensor), lighting hardware, and circuits that support the operation of the aforementioned hardware to acquire images and/or video.

The test application 108 includes an information collection and instruction module 320 (hereinafter "information module 320") that can retrieve user information and provide information and/or instructions to the user. For example, the information module 320 may generate GUIs (e.g., FIGS. 5A-5F) that collect user information before the redness and visual acuity tests are performed by the test application 108. The information module 320 may also provide information and instructions to the user associated with taking the upcoming eye tests. Although the information module 320 may provide and collect information before the user takes the eye tests, the information module 320 may provide and collect information at any time.

The test application 108 includes a redness test module 322 that assists the user in performing an eye redness test. The redness test module 322 can generate GUIs for performing the eye redness test, such as GUIs instructing the user how to hold the user device 100 during the test. The redness test module 322 may also acquire video/images during the eye redness test and instruct the user to perform specific actions (e.g., "Please look up" of FIG. 6C) during the eye redness test.

The test application 108 includes a vision test module 324 that assists the user in performing the visual acuity test. For example, the vision test module 324 can generate GUIs that assist the user in finding the proper testing distance along with a vision chart for the user to read during the visual acuity test. The vision test module 324 may also acquire video/images during the visual acuity test and instruct the user to perform specific actions during the vision acuity test.

The image acquisition functionality associated with the redness test module 322 and the vision test module 324 may be performed by native OS libraries on the user device 100 outside of the test application 108, by code included in the test application 108 (e.g., the modules themselves), and/or a combination of native OS libraries and code included in the test application 108. Image acquisition techniques may vary based on the platform of the user device (e.g., operating system and/or device type). In general, images may be acquired via native operating system methods, frameworks, or libraries that interact with the operating system. In one specific example for IOS®, video frames may be accessed using the AVCaptureVideoDataOutputSampleBufferDelegate method and captureOutput:didOutputSampleBuffer:fromConnection, which is part of the AVFoundation framework that may be included with IOS®. With respect to ANDROID®, the onPreviewFrame callback provided in the Camera.PreviewCallback interface in the android.hardware package can be used. With respect to web browsers, a live video stream can be set up (e.g., using Web Real-Time Communication or a dedicated media streaming server) and be rendered to a canvas by calling drawImage on a CanvasRenderingContext2D object.

The test application 108 includes a shopping module 326 that the user may use to purchase items after taking the eye redness test and/or the visual acuity test. For example, the shopping module 326 may generate GUIs that a user may use to select contact lenses from one or more of the shopping servers 122. For example, using the test application 108 (e.g., the shopping module 326), the user may use a doctor's prescription to purchase the appropriate contact lenses. The prescription can include the parameters and brand of the contact lenses, as well as any other metadata (e.g., required by state law). Contact lens parameters may include, for each eye, Base Curve, Sphere, Cylinder, Axis, Add., Prism, Diameter, and sometimes color. Example metadata can include issuing state, the prescribing doctor's name signature and license number, address of the doctor's office, issue date, and expiration date.

The test application 108 stores application data 328 associated with the test application 108. Example application data 328 may include user information or other information collected by the information module 320. Application data 328 may also include redness test data and vision test data generated by the redness test module 322 and the vision test module 324, respectively. The user information (or other information), redness test data, and vision test data may be referred to herein generally as "eye test data." In some cases, the application data 328 may include data received from the eye test system 102, such as data included in the physician response (e.g., prescription data).

The test system 102 includes a server eye test module 330 (hereinafter "server test module 330") that communicates with the test application 108. For example, the server test module 330 may receive data from the test application 108, such as user information, redness test data, and vision test data. The server test module 330 can store the received data in the system data store 332. In some implementations (e.g., see FIG. 14), the server test module 330 may include some functionality associated with the vision test module 324, such as feature detection (e.g., eye and/or pupil detection) and interpupillary distance determination. In these implementations, the test application 108 may offload some features of the vision test onto the server test module 330.

The test system 102 includes a physician interface module 334 that interfaces with physician devices 104. The physician interface module 334 may generate GUIs for the physicians and transmit eye test data to the physician devices 104 for review. For example, the physician interface module 334 may generate GUIs for evaluating the eye test data, such as GUI elements that present audio, video, and/or images of the user taking the redness and visual acuity tests. Additionally, the GUIs may show the test chart(s) presented to the user during the visual acuity test. The physician interface module 334 may also receive physician response data and store the data in the system data store 332. Example physician response data may include, but is not limited to, the physician name, approval or disapproval of the tests, reasons for the decision, prescription data, and additional notes.

The test system 102 includes a prescreening module 336. The prescreening module 336 may generate GUIs that operators (e.g., employees) of the test system 102 may use to prescreen received eye test data. For example, the operators may screen for completed user information, check the quality of the audio/video associated with the tests (e.g., proper lighting in the images/videos and proper sound acquisition), determine whether the user is at the proper distance, and screen for other factors. If the eye test data is not satisfactory, then the operator may notify the user that the user should retake one or more of the eye tests. Such a prescreening functionality may ensure quality eye test data that optimizes the physician's time.

Note that FIG. 3, FIG. 12, and FIG. 14 include arrows illustrating communication between modules. Some arrows have been omitted for illustration purposes (e.g., in order to simplify the figures).

Figure 4:
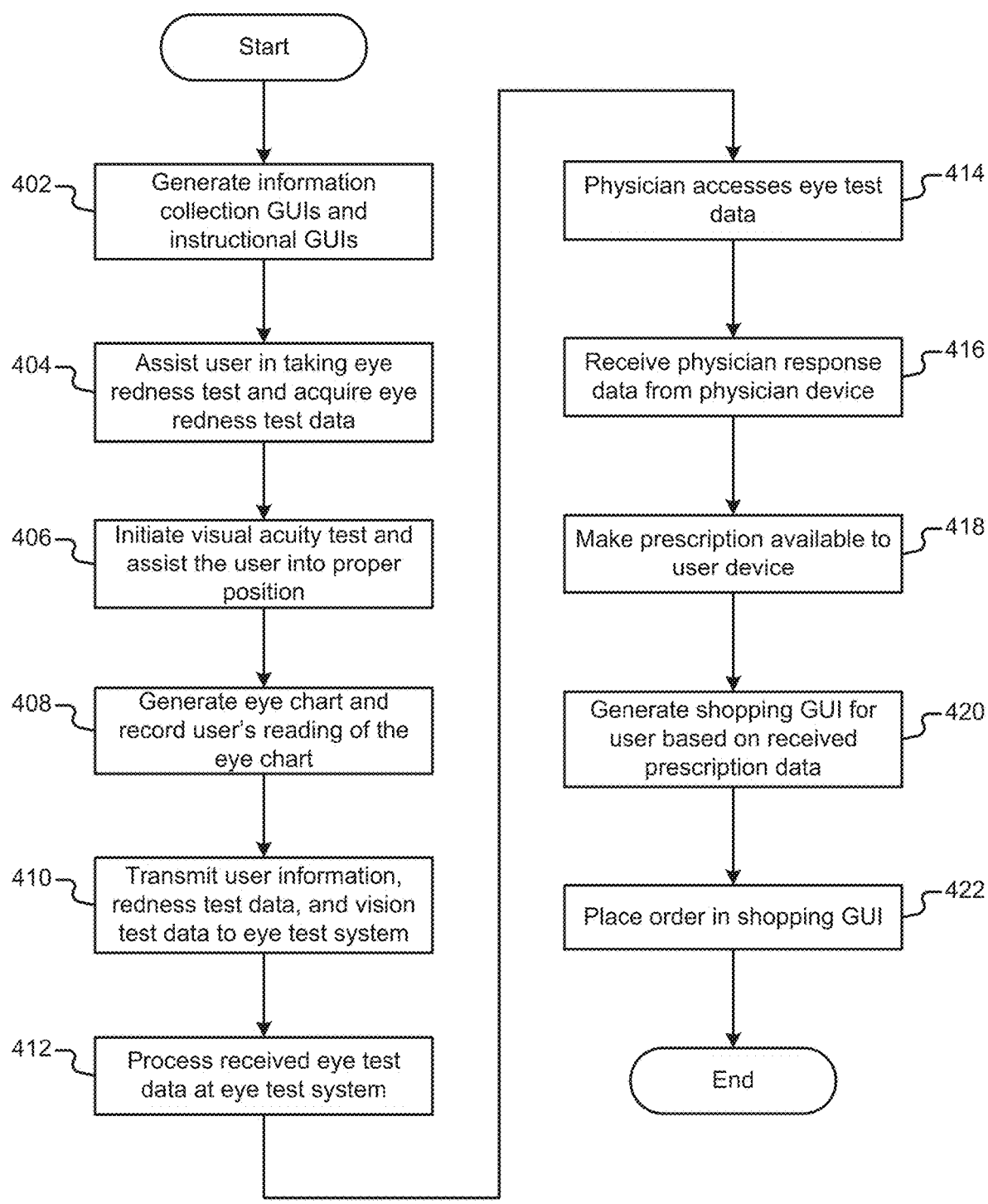
FIG. 4 is a flow diagram of another example method for performing eye examinations using an eye test application and an eye test system.

FIG. 4 illustrates an example method describing operation of an example test application 108. The method of FIG. 4 references the example test application modules of FIG. 3. The method of FIG. 4 also references example GUIs (see FIGS. 5A-9C) that may be generated by the test application.

Upon starting the test application 108, the information module 320 generates GUIs for collecting user information and providing instructions in block 402. FIGS. 5A-5F illustrate various GUIs that the information module 320 may generate prior to the eye tests. In FIG. 5A, the information module 320 prompts the user to enter user information, such as the user's email address, state of residence, age, and date of last dilated eye exam. In FIG. 5B, the information module 320 provides preliminary instructions for the user before beginning the eye tests. Specifically, the GUI instructs the user to ensure that they are wearing contacts (e.g., their current prescription lenses), have 10 feet of space for the test, and are in a well-lit room.

In FIGS. 5C-5F, the information module 320 presents a series of questions before the eye tests. The user may respond to the questions (e.g., Yes/No). The specific questions are tailored to determine: 1) whether the user sees clearly in their contact lenses, 2) whether the user has any pain or discomfort in their contact lenses, 3) whether they understand that the test they are taking is a vision test, and is not a substitute for a dilated eye health exam, and 4)

whether the user has any of a list of health concerns, such as cataracts, color blindness, eye pain, etc. The information collected by the information module 320 (e.g., in FIGS. 5A-5F) can be submitted to the test system 102 for physician review.

Figure 6A:
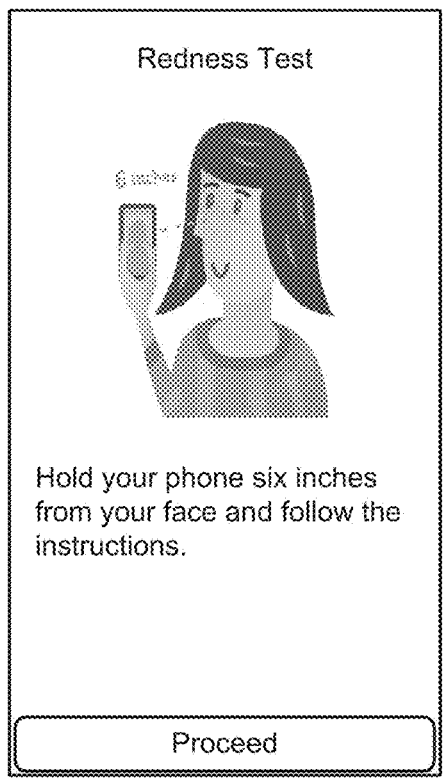
FIGS. 6A-6D illustrate example GUIs used to assist a user in performing an eye redness test.

In block 404, the redness test module 322 assists the user in taking the eye redness test and acquires eye redness test data. FIGS. 6A-6D illustrate various GUIs that the redness test module 322 may generate to assist the user in taking an eye redness test. Initially, as illustrated in FIG. 6A, the redness test module 322 generates a GUI that instructs the user to hold the user device 100 near their face (e.g., 6 inches from their face). The GUI includes a button GUI element with a direction to "Proceed." The user may select (e.g., touch/click) the button GUI element to proceed with the eye redness test.

Figure 6B:
Figure 6C:
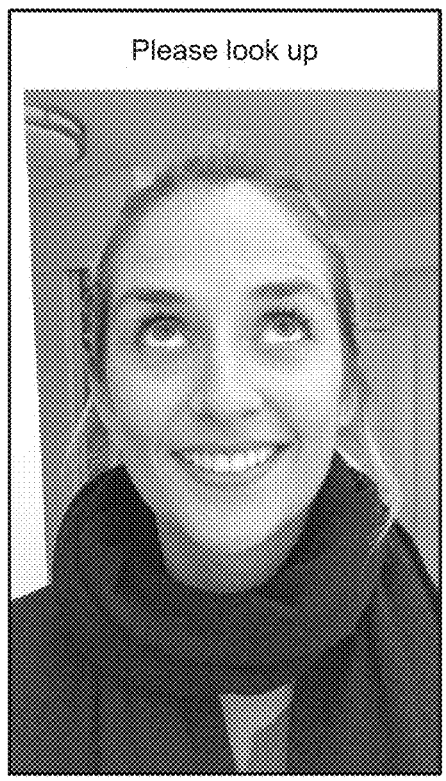
Figure 6D:
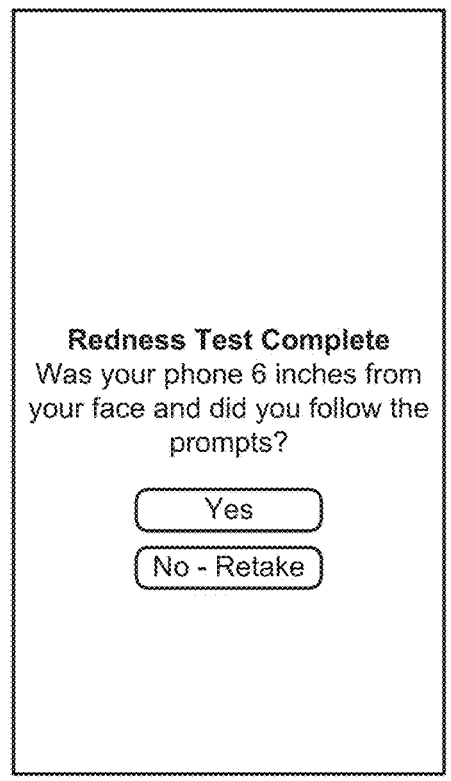

The redness test module 322 may then generate GUIs that display the user's face and eyes (see FIGS. 6B-6C). For example, the redness test module 322 may acquire video/images from a front facing camera 300 on the user device 100. The redness test module 322 may display the acquired video/images to the user on the display 302 along with additional instructions. As illustrated in FIG. 6C, the additional instructions may instruct the user to "Please look up." When the user is looking up, the physician can assess any visible signs of redness, irritation, or disease in the patient's eye and eyelid. The physician may also assess the quality and range of eye movement.

The redness test module 322 may acquire the video and/or images of the user while the user is taking the eye redness test. For example, the redness test module 322 may acquire the video and/or images of the user while they are looking up. Upon completion of the eye redness test (e.g., after looking up), the user may be prompted to indicate whether they performed the test properly (e.g., see FIG. 6D). The user may select the "Yes" GUI button to complete the test or select the "No—Retake" GUI button to retake the test.

After completion of the eye redness test, the user device 100 may store the redness test data and/or transmit the redness test data to the test system 102 for later review by the physician. The redness test data may include the video and/or images of the user taking the eye redness test. The physician may use the video and/or images to determine how the user's contact lenses sit on the user's eyes and also to ensure there are no signs of inflammation.

In block 406, the vision test module 324 initiates the visual acuity test and assists the user into the proper position. For example, the vision test module 324 may generate a GUI that instructs the user to stand at the testing distance. The vision test module 324 then calculates the user's distance from the user device 100 and generates GUIs that assist the user into the proper position. The GUIs may include a number (e.g., in feet or meters) that indicates the user's distance from the user device 100. After the user is positioned at the testing distance, the vision test module 324 may generate an eye chart GUI and record the user's reading of the eye chart in block 408.

Figure 7C:
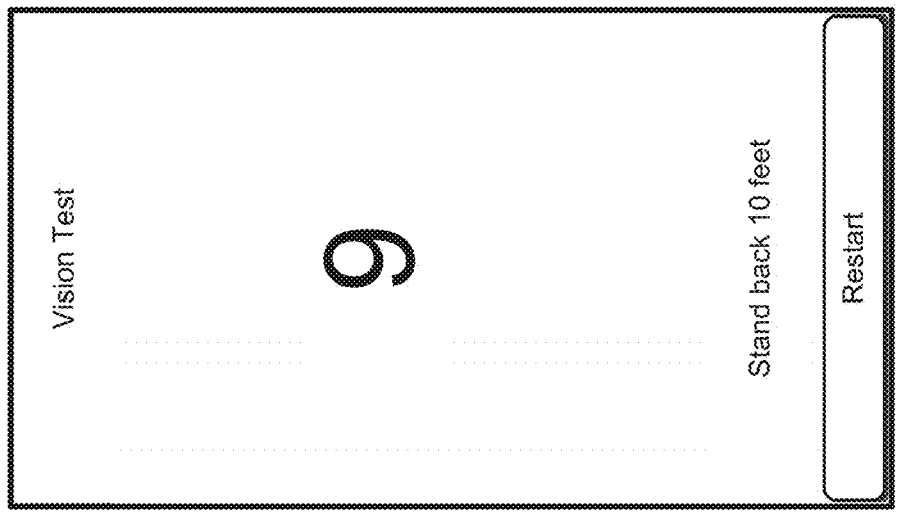
FIGS. 7A-7C illustrate example GUIs used to assist a user into the proper testing position for a visual acuity test.
Figure 7B:
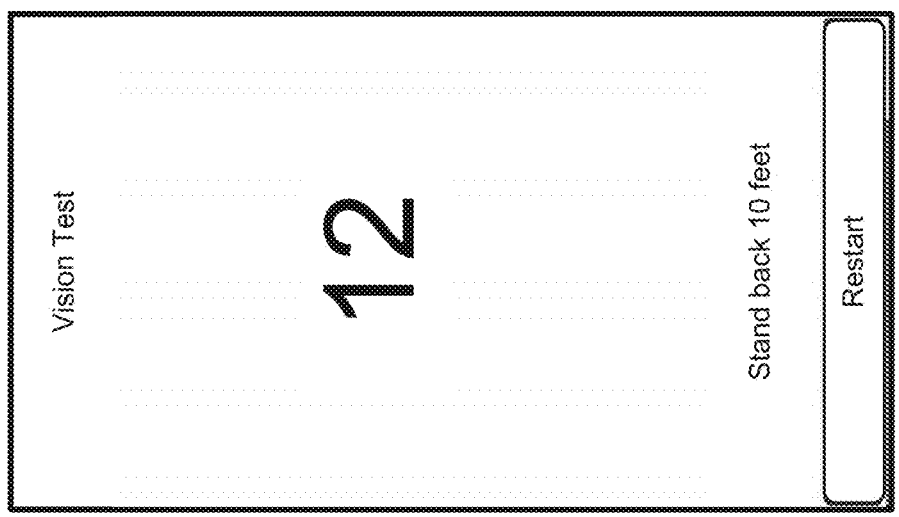
Figure 7A:
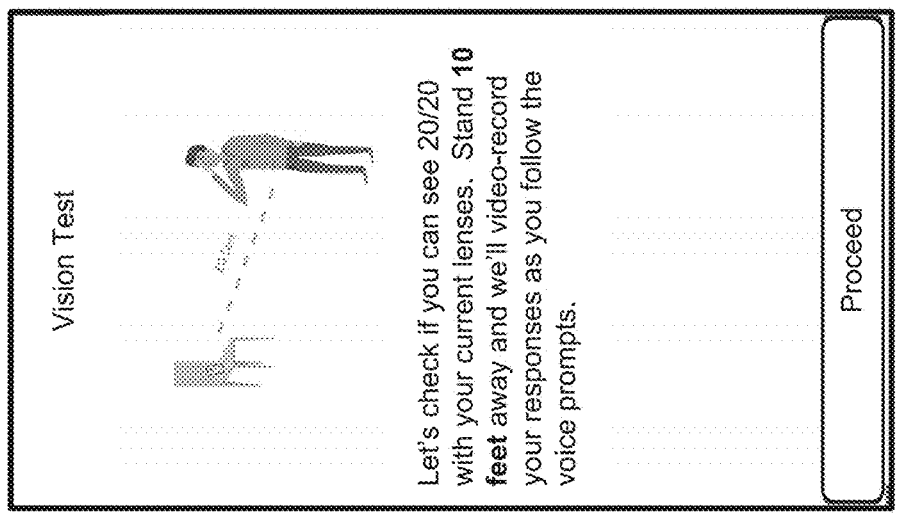

FIGS. 7A-7C illustrate various GUIs that the vision test module 324 may generate in order to assist the user in finding the proper position for taking the visual acuity test. In FIG. 7A, the GUI notifies the user that they should stand at the appropriate testing distance for taking the visual acuity test. The testing distance is described hereinafter as 10 ft, although the test application 108 and the test system 102 may be configured to operate in a similar manner described herein for other testing distances.

While viewing the GUI of FIG. 7A, the user may place the user device 100 on a stationary object and press a GUI button to proceed. After pressing the button to proceed, the vision test module 324 may generate a GUI that displays the user's current distance from the user device 100 along with the instructions to stand back 10 ft. In FIG. 7B, the GUI indicates to the user that they are standing 12 ft from the user device 100. In response to the indication, the user may approach the user device 100. FIG. 7C illustrates a GUI in which the user is standing too close to the user device 100 (e.g., at 9 feet). In response to the indication that the user is 9 feet from the user device 100, the user may step back from the user device 100 to reach the desired 10 ft distance.

Although the figures illustrate how the test application 108 can update distance numbers on the GUI, in other implementations, the user device 100 (e.g., according to the test application 108) may provide additional, or alternative, types of feedback to the user to aid the user in finding the proper testing distance. In one example, the GUI may display commands to the user indicating that the user should come closer to the user device 100 or move away from the user device (e.g., "Approach" or "Move back"). In another example, the test application 108 may provide audio cues to the user (e.g., via the speaker 304) to indicate how the user should be positioned. For example, the test application 108 may provide audio cues indicating the distance between the user and the user device 100 (e.g., the measurement in feet). As another example, the test application 108 may provide audio cues including instructions for the user to follow, such as "back up" or "move forward."

The test application 108 may provide a variety of visual and audio cues when the user has reached the correct testing position. For example, the GUI may display 10 ft when the user has reached the correct position. The GUI may also display text indicating that the user has reached the correct position and that the user should remain in the position for the visual acuity test. As another example, the GUI may change colors when the user has reached the correct position. For example, the GUI may flash a green color to indicate that the user has reached the proper testing distance (e.g., 10 ft). In some implementations, the test application 108 may provide audio cues to the user indicating that the user has reached the correct distance and that the user should maintain the position for the subsequent visual acuity test.

FIGS. 8A-8B illustrate example GUIs generated by the vision test module 324 during the visual acuity test. In FIG. 8A, the test application 108 displays the visual acuity test eye chart. The chart includes a row of darkened letters for the user to read out loud (e.g., C, Z, K, and R). The vision test module 324 may appropriately size the letters for the test based on parameters of the user device 100 (e.g., the display size and display resolution). In one example, the letters may be sized so that a user having 20/20 vision can read the letters at a distance of 10 ft. In a specific example, the letters may be approximately 4.5 mm tall on the display, although letters of different sizes may be rendered, depending on the testing distance. The test application 108 and/or the test system 102 may store a list of screen sizes/resolutions for a variety of types of user devices 100 which may be used by the vision test module 324 to determine the rendered size of the letters used in the visual acuity test. The vision test module 324 may also query the operating system for screen sizes and resolutions on some user devices.

In general, the test application 108 will direct the user to test each of their eyes independently (e.g., by covering one eye). The user may also be directed to test both eyes (e.g., without covering). The test application 108 may provide audio cues to the user to indicate that the user should cover an eye and read the letters presented on the display. In some implementations, the test application 108 may provide the instructions as text on the screen.

The vision test module 324 may record video and audio of the visual acuity test as the user is taking the test. For example, the vision test module 324 may record video and audio of the user covering/uncovering their eyes and reading the presented text. The test application 108 may provide the video/audio recording and corresponding exam chart (e.g., the correct characters) to the test system 102 so that the physician can review the video test along with the exam chart. In some implementations, the vision test module 324 may generate random characters for the visual acuity test so that the user is prevented from memorizing the test characters.

FIG. 8B illustrates a GUI generated by the vision test module 324. The GUI includes a prompt that indicates to the user that the vision test is complete. The user may interact with the GUI to retake the visual acuity test or indicate that the test was appropriately finished. For example, the user can select the "No—Retake" GUI button to retake the test. Alternatively, the user can select the "Yes" GUI button to indicate the test was appropriately finished. If the user indicates that the test was appropriately finished, the test application 108 may store the vision test data on the user device 100 and/or submit the vision test data to the test system 102 for physician review.

Referring back to FIG. 4, the test application 108 transmits the information collected by the information module 320, the eye redness test data, and the vision test data to the test system 102 in block 410. The eye redness test data may include, but is not limited to, video and/or images of the user taking the eye redness test. The vision test data may include, but is not limited to, video, images, and/or audio of the user taking the visual acuity test, along with vision charts associated with the visual acuity test.

In block 412, the test system 102 (e.g., the server test module 330) processes the eye test data received from the test application 108. For example, the server test module 330 may format and store the received eye test data in the server data store 332 for later use. In some implementations, an operator (e.g., employee) of the test system 102 may pre-screen the received eye test data before the data is made available to a physician for review.

In block 414, the physician accesses the eye test data via the physician interface module 334. In block 416, the physician provides a physician response (e.g., a prescription) to the test system 102 after reviewing the eye test data. In block 418, the test system 102 makes the prescription available to the user device 100. For example, the test system 102 may transmit the prescription to the user device 100 and/or email the prescription to the user. The user may use the received prescription to purchase contact lenses. For example, in block 420, the shopping module 326 generates a contact lens shopping GUI for the user based on the received prescription data. The shopping module 326 may access one or more shopping servers 122 and present a variety of contact lenses to the user for purchase. In some implementations, the shopping module 326 may filter the available lenses according to the prescription. In block 422, the user may place an order for contact lenses in the shopping GUI. Although the user may place the order for contact lenses after receiving a prescription, in some implementations, the user may place the order before the prescription is confirmed, which may result in a cancellation of the order if the prescription is denied.

FIGS. 9A-9C illustrate example shopping GUIs that the test application 108 may display after completion of the visual acuity test and receipt of a prescription. In FIG. 9A, the GUI confirms that the user has completed the eye redness test, the visual acuity test, and signed a waiver. The GUI also prompts the user to proceed with purchasing contacts using the test application 108. For example, the GUI button prompts the user to "Search for my brand" of contact lenses. In FIGS. 9B-9C, the user can select various contact lenses. The user may purchase the selected contact lenses and have the lenses shipped to their home address. Example lenses illustrated in FIGS. 9B-9C include a variety of Acuvue® brand contact lenses and Air Optix® brand contact lenses.

Figure 10:
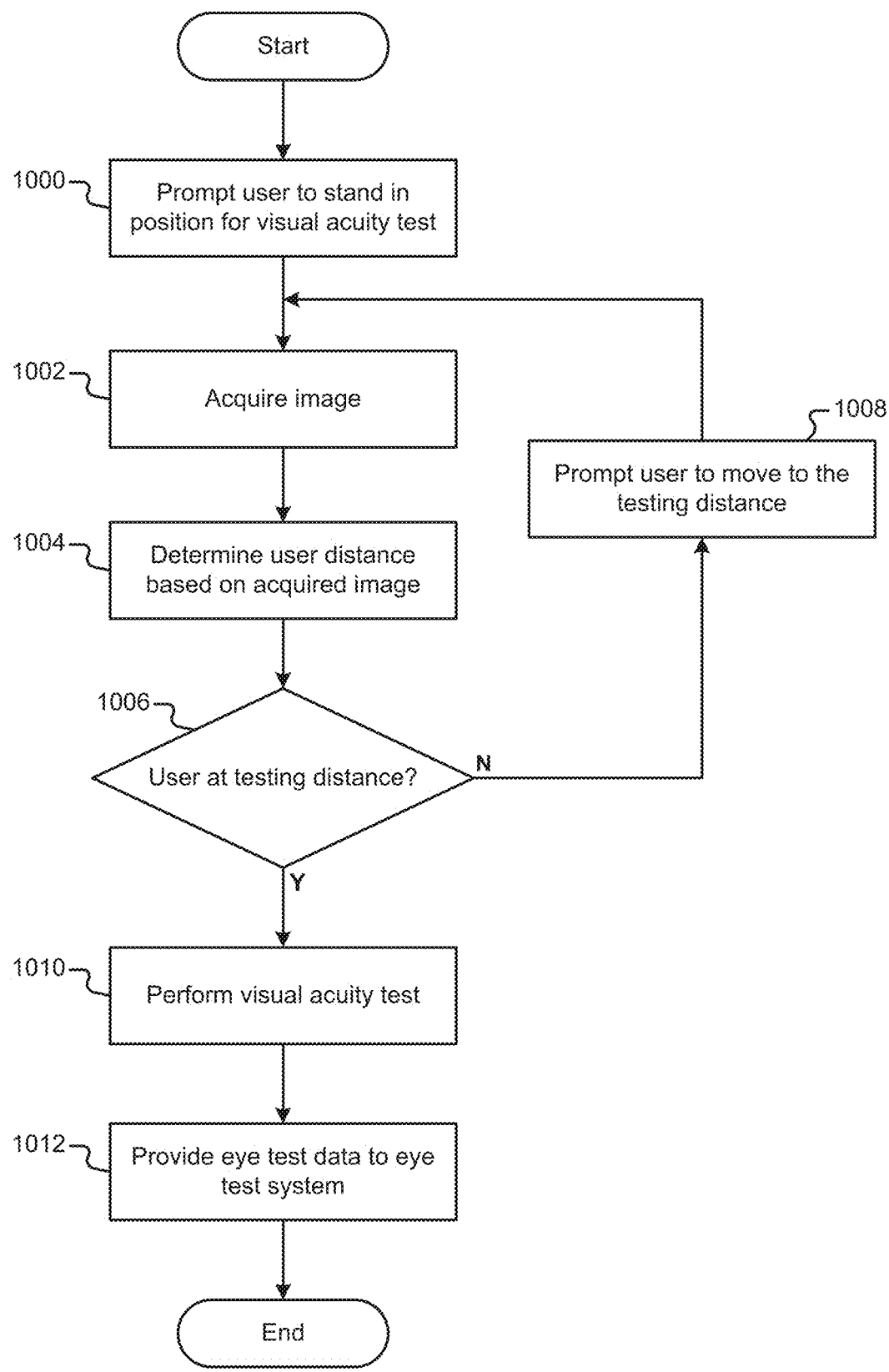
FIG. 10 is a flow diagram of an example method for providing a visual acuity test.

FIG. 10 illustrates an example method for assisting a user in taking a visual acuity test. Initially, in block 1000, the vision test module 324 prompts the user to stand in position for the visual acuity test (e.g., see FIG. 7A). The user may then proceed with attempting to find the correct position for the visual acuity test with assistance from the user device 100 (e.g., visual/audio assistance).

In block 1002, the vision test module 324 acquires an image of the user (e.g., using the camera 300) as the user is finding the testing position. In block 1004, the vision test module 324 determines the distance of the user from the user device 100 based on the acquired image. For example, the vision module 324 may determine the user's distance based on the user's interpupillary distance (IPD), a predetermined IPD value associated with a population of individuals, and other factors described with respect to FIG. 11. In block 1006, the vision test module 324 determines whether the user is at the proper testing distance. If the vision test module 324 determines that the user is not at the proper testing distance, the vision test module 324 may prompt the user to move to the proper testing distance in block 1008 (e.g., FIGS. 7B-7C). The vision test module 324 may then acquire another image of the user and determine the distance of the user from the user device 100 based on the acquired image in blocks 1002-1004. In some implementations (e.g., FIG. 14), the user device 100 may transmit data (e.g., acquired images) to the test system 102 for processing in order to determine the distance of the user from the user device 100. The user device 100 and/or the test system 102 may continue to acquire images (e.g., pictures and/or video) and determine the distance of the user based on the acquired images until the user is at the proper testing distance.

If the vision test module 324 determines that the user is at the proper testing distance in block 1006, the vision test module 324 may initiate the eye chart portion of the visual acuity test in block 1010 (e.g., as described with respect to FIGS. 8A-8B). In some implementations, the vision test module 324 may record video and audio of the user taking visual acuity test. After finishing the visual acuity test, the test application 108 may submit the eye test data to the test system 102 in block 1012.

As described herein, the test application 108 (e.g., the vision test module 324) and/or the test system 102 (e.g., the sever test module 330) may determine the distance of the user from the user device 100 based on an acquired image (e.g., a single image and/or video). FIG. 11 is a diagram that graphically illustrates how the test application 108 and/or the test system 102 may determine the distance of the user from the user device 100 based on the acquired image and the user's IPD value.

In FIG. 11, a stylized image of a user's face 1100 and eyes 1102 is illustrated within a box that represents the user's surrounding environment 1104 to be captured within an image. Each of the user's eyes 1102 includes dark dots that represent the user's pupils. Opposite to the user's face, at a distance d, is the camera lens 1106 of the user device 100. The user device 100 captures the image 1108 of the user's face 1100 and eyes 1102 on the opposite side of the camera lens 1106.

The illustration, annotations, and equations in FIG. 11 describe how the test application 108 and/or the test system 102 may determine the user distance based on the acquired image 1108 and some additional data related to the user device 100. Determination of the distance d between the camera 300 and the user is now described with respect to FIG. 11.

The acquired image 1108 includes the user's face and eyes. The acquired image 1108 has a width of L2, in terms of pixels. The image width L2 (in pixels) may be determined based on analysis of the acquired image 1108 and/or based on camera specifications associated with the user device. The field of view (FoV) of the camera, illustrated as theta ($\Theta$), can also be determined based on camera specifications associated with the user device 100. The user device 100 may provide the various camera specifications to the vision test module 324 in some examples. In other examples, the test system 102 may store the camera specifications (e.g., width L2 in pixels and/or $\Theta$), which may be retrieved by the test application 108. The focal length (f) may then be determined based on L2 and $\Theta$, for example, using the equation $f = L2/(2*\tan(\Theta/2))$, as illustrated in FIG. 11.

The user device 100 and/or the test system 102 may process the acquired image to determine the IPD distance L1 in terms of pixels. For example, the user device 100 and/or the test system 102 may identify the user's face and the user's eyes/pupils in the acquired image and then determine the number of pixels between the user's pupils. The test application 108 and/or the test system 102 may include a stored IPD value (e.g., predetermined IPD value), referred to in FIG. 11 as the median IPD. The median IPD may be a distance value in actual length (e.g., in millimeters, inches, or feet) that corresponds to an approximate distance between the user's pupils. The median IPD value may be based on measured IPD values within the population (e.g., a plurality of people other than the user), and may be selected such that it represents a median IPD value among the population (e.g., with a low standard deviation within the population). As such, the median IPD can be utilized as the IPD value for a plurality of users. In one example, a median IPD of approximately 63 mm may be used (e.g., 63.36 mm). If a median IPD is in the units of millimeters, the output distance may also be in units of millimeters.

Although a median IPD value of a population may be used, other IPD values associated with the population may be chosen. For example, a mode or average IPD value may be used, assuming the value(s) can provide sufficient calculation of user distance. In some cases, the mode value in the population may be similar to the median value in the population. Predetermined IPD values may also be stored based on several demographic factors including age, sex, and race. In this case, the user may specify age, sex, and/or race, which can be used for selection of the IPD values. In some implementations, the test application may use a linear regression or classifier to better predict the IPD of a patient using a combination of any of these factors. In other implementations, the test application may ask the user to specify their measured IPD. For example, the user may specify their measured IPD (e.g., as measured by a doctor), which may be included on their external glasses or contact lens prescription in some cases.

The mathematical model in FIG. 11 may use a variety of assumptions. For example, the pinhole camera model may be used, which may simplify the aperture of the camera 300 to be a single point, and which may also assume no lenses focus or distort the image. Because of this simplification, triangle A and triangle B may be said to be "similar triangles." Additionally, it may be assumed that the user is staring directly at the camera 300. For example, it may be assumed that the plane that intersects the user's eyes 1102 is orthogonal to the vector defined from the aperture of the camera to the point between the user's eyes 1102.

The test application 108 and/or the test system 102 may determine the distance between the user and the user device 100 based on the values determined above. For example, the test application 108 and/or the test system 102 may determine the distance d between the user and the user device 100 using the following equation: $d = (\text{median IPD}) * f / L1$. The user device 100 may report this distance to the user (e.g., FIGS. 7B-7C) in order to assist the user in finding the proper testing distance.

FIGS. 12-13 illustrate an example vision test module 324 and a more detailed example method for assisting a user in taking a visual acuity test. The method of FIG. 13 is described with respect to the example vision test module 324 of FIG. 12. Initially, in block 1300, the vision test module 324 prompts the user to stand in position for the visual acuity test (e.g., see FIG. 7A). The user may then proceed with attempting to find the correct position for the visual acuity test with assistance from the vision test module 324 (e.g., visual/audio assistance).

In block 1302, the image acquisition module 1200 acquires an image of the user from the camera 300 and the image acquisition hardware 316 as the user is finding the testing position. In block 1304, the feature detection module 1202 process the acquired image to detect the user's pupils. For example, the feature detection module 1202 may identify the user's face in the acquired image and then identify the user's eyes/pupils in the acquired image. The feature detection module 1202 may detect facial regions in an image or video frame using a trained classifier (e.g., a trained histogram of oriented gradients (HOG) identifier) or Convolutional Neural Network. The feature detection module 1202 may then detect facial landmarks including pupils, within each facial region of interest, using another trained classifier (e.g., an ensemble of regression trees). In some implementations, the feature detection module 1202 may detect the user's pupils locally (e.g., using local processing on the user device). In other implementations (e.g., FIG. 14), the user device 100 may transmit the acquired image to the test system 102, and the test system 102 may process the acquired image to identify the user's pupils.

In some implementations, the feature detection module 1202 may detect the user's eyes and then estimate the location of the user's pupils within the user's eyes. For example, the feature detection module 1202 may detect the user's eyes and set the user's pupil location at the center of the eyes. As another example, the feature detection module 1202 may detect multiple points around the border of where the eyelid opens and then calculate the position of the pupil based on the multiple points (e.g., by calculating an average position).

In block 1306, the IPD determination module 1204 determines the user's IPD distance in pixels and the width of the image L2 in pixels. In block 1308, the user distance module 1206 determines the distance of the user d based on the median IPD value, the IPD in pixels, the image width L2 in pixels, and the camera FoV, as described with respect to FIG.

11. In block 1310, the user distance module 1206 displays the calculated user distance to the user on the display 302.

In block 1312, the user distance module 1206 determines whether the user is at the proper testing distance. If the user is not at the proper testing distance, the user distance module 1206 may prompt the user to move to the proper testing distance in block 1314 (e.g., FIGS. 7B-7C). The image acquisition module 1200 may then acquire another image, which can be processed to determine the user distance in blocks 1304-1308. If the user is at the proper testing distance, the chart generation module 1208 may generate the chart(s) for the visual acuity test in block 1316 (e.g., as described with respect to FIGS. 8A-8B). The vision test recording module 1210 may record the user while the user is finding the proper testing distance and taking the visual acuity test.

The vision test module 324 includes a capabilities assessment module 1212 (hereinafter "assessment module 1212") that may assess the capabilities of the user device's hardware and/or software. For example, the assessment module 1212 may determine camera properties, such as FoV and image capture dimensions (e.g., image width). The assessment module 1212 may also determine other user device properties, such as display size and display resolution. Additionally, the assessment module 1212 may determine whether the user device 100 is capable of feature detection, such as face detection, eye detection, and/or pupil detection. The assessment module 1212 may also determine the network connection speed between the user device 100 and the test system 102. In some cases, the assessment module 1212 can retrieve the information related to the user device 100 from the application data 328 and/or the system data store 332. Additionally, or alternatively, the assessment module 1212 may query the user device 100 to determine properties of the user device 100. In some implementations, the assessment module 1212 can also determine whether the user granted permissions to access the camera and microphone. The assessment module 1212 may also assess the level of volume to ensure that instructions can be heard.

The assessment module 1212 can be configured to query the operating system for screen sizes and resolutions on some user devices (e.g., for specific user devices listed in the app data 328). The app data 328 may also include the screen size/resolution for a variety of specified user devices. For a web-based implementation, since screen resolution varies among user devices, and programmatic access to the screen size/resolution may be inaccessible, the assessment module 1212 may ask the user to perform a set of steps for determining screen size/resolution. For example, the user may be prompted to place an object of known size (e.g., a credit card) over a resizable object (e.g., a resizable credit card) on the display. Then the user can resize the object to fit the known size object. Using this data, the assessment module 1212 may map a fixed width (e.g., card width) to a number of pixels, and then calculate the requisite size of the letters based on this mapping.

FIG. 14 illustrates an implementation of the test application 108 and the test system 102 in which the test application 108 offloads some processing to the test system 102. Specifically, the vision test module 324 offloads the functionality of the feature detection module 1202 and the IPD determination module 1204 to the system feature detection module 1400 and the system IPD determination module 1402. For example, the vision test module 324 may access the functionality of the modules 1400, 1402 via an application programming interface (API) provided by the test system 102. Note that the feature detection module 1202 and the IPD determination module 1204 have been renamed as the device feature detection module 1202 and the device IPD determination module 1204 in FIG. 14 to differentiate the modules 1202, 1204 from the modules 1400, 1402 included in the test system 102.

The system feature detection module 1400 and the system IPD determination module 1402 may perform similar functions as the device feature detection module 1202 and the device IPD determination module 1204, respectively. The functionality may be offloaded from the user device 100 to the test system 102 for a variety of reasons. In some cases, the user device 100 may lack sufficient hardware/software computing resources to provide the functionality associated with the device feature detection module 1202 and the device IPD determination module 1204. For example, the user device 100 may lack sufficient processing power and/or the proper software libraries to implement the functionality associated with the device feature detection module 1202 and the device IPD determination module 1204. The assessment module 1212 may determine whether the user device 100 includes sufficient hardware/software computing resources to provide such functionality. If the user device 100 does not include sufficient computing resources, the vision test module 324 may offload the functionality of the device feature detection module 1202 and the device IPD determination module 1204 to the test system 102, as illustrated in FIG. 14.

In some implementations, processing tasks on the user device 100 and the test system 102 may vary based on internet connection speed between the user device 100 and the test system 102, as determined by the assessment module 1212. For example, for faster network connections (e.g., greater than a threshold network speed), the user device 100 may offload the image processing to the test system 102 by transmitting the videos/images to the test system 102 for processing. On the other hand, if the network connection is slow (e.g., less than a threshold network speed), the user device 100 may attempt to minimize the data transmitted to the test system 102 via the network 106 (e.g., by compressing the videos and/or cropping/masking the images).

Although the vision test module 324 includes the device feature detection module 1202 and the device IPD determination module 1204 in FIG. 12 and FIG. 14, in some implementations, the vision test module 324 may not include the modules 1202, 1204. Instead, the vision test module 324 may be configured to use the test system 102 to provide the functionality attributed to the modules 1202, 1204.

In some cases, the distance determination may be subject to some uncertainty when using the median IPD, since IPD may deviate among users. The user device 100 and/or the test system 102 may determine a confidence score associated with the determined distance that reflects a level of confidence in the distance. For example, it may represent a statistical confidence that the patient is 10 feet or greater away from the camera. The confidence score may be included in eye test data that is reviewed by the physician. The user device 100 and/or the test system 102 may compute the confidence score in the following manner. The user device 100 and/or test system 102 may determine a test IPD value (e.g., in actual distance) based on the measured IPD in pixels. The test IPD may be the IPD that the user would have to have in order to be a target distance away from the user device 100 (e.g., 10 ft). The user device 100 and/or the test system 102 may then use a complementary cumulative distribution function (e.g., a tail function) to compute the probability that a human could have an IPD greater than or equal to the test IPD. The computed probability may indicate the probability that the user is greater than or equal to the target distance. In a specific example, a user standing an unknown distance from the camera may have to have a hypothetical IPD of 60 mm in order to be at least 10 feet away. In this case, the computation may return a confidence value of 0.81, indicating that there is an 81% probability that the user is at least 10 feet away.

Although the user device 100 and/or the test system 102 may use a single median IPD value across a plurality of users, in some implementations, the user device 100 and/or the test system 102 may determine an IPD value specifically for the user. For example, the user device 100 and/or the test system 102 may analyze an image to determine user characteristics, such as the age, sex, and/or race. The user device 100 and/or the test system 102 may then determine an IPD value for the particular user based on the determined age, sex, and/or race. For example, the user device 100 and/or the test system 102 may select a different IPD value from a set of IPD values associated with the determined characteristics and/or modify the median IPD value based on the determined characteristics. In these implementations, the user-specific IPD value may be more accurate than the median IPD value.

The user device 100 and/or the test system 102 may implement alternative techniques for determining the distance between the user and the user device 100. For example, the user device 100 and/or the test system 102 may implement a trained classifier to determine the distance between the user device 100 and the user. The trained classifier may be trained on a variety of faces at representative distances to the user. In these implementations, the classifier may take as input a series of images and/or a snapshotted video. The classifier may then return a distance based on the inputted images. The user device 100 and/or the test system 102 may implement the classifier as an alternative to the IPD determination described in FIG. 11. In other implementations, the user device 100 and/or the test system 102 may use the classifier in addition to the IPD determination described in FIG. 11 (e.g., as a check on the IPD distance calculation).

Although the distance determination is described herein as being used for the visual acuity test, in some implementations, the user device 100 and/or the test system 102 may determine the distance between the user and the user device 100 for other eye tests, such as the eye redness test. In these implementations, the user device 100 and/or the test system 102 may determine the user distance based on the median IPD and/or another technique (e.g., using a trained classifier).

In some implementations, the user device 100 and/or the test system 102 may be configured to identify the user among other people and objects included in the acquired image. Put another way, the user device 100 and/or the test system 102 may isolate the user from other people and/or objects in the acquired image. For example, the user device 100 and/or the test system 102 may independently track the user in the image so that the user can properly take the eye tests in the presence of others.

As described herein, the user device 100 (e.g., according to the test application 108) and/or the test system 102 may provide functionality associated with providing eye tests. Put another way, the user device 100 (e.g., the test application 108) and the test system 102 may share in providing the eye testing functionality described herein. Accordingly, functionality attributed herein to the user device 100 and/or the test system 102 may be provided individually by either the user device 100 or the test system 102 or shared among the user device 100 and the test system 102. Division of the various functions among the user device 100 and/or the test system 102 described herein may vary depending on factors described herein, or for other reasons.

The modules and data stores described herein may be embodied by electronic hardware, software, firmware, or any combination thereof. Depiction of different features as separate modules and data stores does not necessarily imply whether the modules and data stores are embodied by common or separate electronic hardware or software components. In some implementations, the features associated with the one or more modules and data stores depicted herein may be realized by common electronic hardware and software components. In some implementations, the features associated with the one or more modules and data stores depicted herein may be realized by separate electronic hardware and software components.

The test system 102 may include one or more computing devices that are configured to implement the techniques described herein. Each of the one or more computing devices may include any combination of electronic hardware, software, and/or firmware described above. For example, each of the one or more computing devices may include any combination of processing units, memory components, and storage devices. The one or more computing devices of the test system 102 may also include various human interface devices, including, but not limited to, display screens, keyboards, pointing devices (e.g., a mouse), touchscreens, speakers, and microphones.

In some examples, the test system 102 may include one or more server computing devices configured to communicate with user devices 100. The one or more computing devices may reside within a single machine at a single geographic location in some examples. In other examples, the one or more computing devices may reside within multiple machines at a single geographic location. In still other examples, the one or more computing devices of the test system 102 may be distributed across a number of geographic locations.

What is claimed is:

1. A non-transitory computer-readable medium comprising computer-executable instructions, the computer-executable instructions causing a processing unit of a user device to:

instruct a user to stand at a visual acuity testing distance away from the user device, wherein the visual acuity testing distance is a predetermined distance away from the user device for taking a visual acuity examination;

acquire an image of the user using a camera;

determine a user interpupillary distance based on the acquired image, wherein the user interpupillary distance indicates a distance between the user's pupils in terms of pixels;

determine a current distance (d) between the user and the user device based on a width of the acquired image in terms of pixels, a field of view of the camera, and the equation d=(IPD)*f/L, wherein IPD is a predetermined interpupillary distance that is representative of a population of people, f is the focal length of the camera in pixels, and L is the user interpupillary distance in pixels;

display the current distance between the user and the user device on a display included on the user device;

display an eye chart on the display in response to the user reaching a distance from the user device that is equal to the visual acuity testing distance;

record a video of the user reading the displayed eye chart at the visual acuity testing distance; and receive a user input indicating that the user has completed reading the displayed eye chart.

2. The computer-readable medium of claim 1, further comprising instructions that cause the processing unit to:

instruct the user to move towards the user device if the determined current distance is greater than the visual acuity testing distance; and instruct the user to move away from the user device if the current determined distance is less than the visual acuity testing distance.

3. The computer-readable medium of claim 1, further comprising instructions that cause the processing unit to:

detect the user's pupils in the acquired image; and determine the user interpupillary distance based on the detected user's pupils in the acquired image.

4. The computer-readable medium of claim 1, further comprising instructions that cause the processing unit to:

detect the user's eyes in the acquired image;

estimate the location of the user's pupils within the user's eyes; and determine the user interpupillary distance based on the estimated location of the user's pupils in the acquired image.

5. The computer-readable medium of claim 1, wherein the predetermined interpupillary distance is an interpupillary distance that is representative of a population of people other than the user.

6. The computer-readable medium of claim 1, wherein the predetermined interpupillary distance is a value that represents a median interpupillary distance among the population.

7. The computer-readable medium of claim 1, further comprising instructions that cause the processing unit to select the predetermined interpupillary distance from a set of interpupillary distances.

8. The computer-readable medium of claim 7, further comprising instructions that cause the processing unit to select the predetermined interpupillary distance from the set of interpupillary distances based on the sex of the user.

9. The computer-readable medium of claim 7, further comprising instructions that cause the processing unit to select the predetermined interpupillary distance from the set of interpupillary distances based on the age of the user.

10. The computer-readable medium of claim 1, further comprising instructions that cause the processing unit to:

transmit the video to a remote eye test system via a network; and receive a prescription from the remote eye test system in response to the transmitted video.

11. The computer-readable medium of claim 1, wherein the camera is included on the user device.

12. The computer-readable medium of claim 1, further comprising instructions that cause the processing unit to generate random characters for the eye chart.

13. A non-transitory computer-readable medium comprising computer-executable instructions, the computer-executable instructions causing a processing unit of a user device to:

instruct a user to stand at a visual acuity testing distance away from the user device, wherein the visual acuity testing distance is a predetermined distance away from the user device for taking a visual acuity examination;

acquire an image of the user using a camera;

transmit the image to a remote eye test system via a network;

receive a user interpupillary distance value from the remote eye test system via the network, wherein the user interpupillary distance value indicates a distance between the user's pupils in terms of pixels;

determine a current distance (d) between the user and the user device based on a width of the acquired image in terms of pixels, a field of view of the camera, and the equation $d=(IPD)*f/L$, wherein IPD is a predetermined interpupillary distance that is representative of a population of people, f is the focal length of the camera in pixels, and L is the user interpupillary distance in pixels;

display the current distance between the user and the user device on a display included on the user device;

display an eye chart on the display in response to the user reaching a distance from the user device that is equal to the visual acuity testing distance;

record a video of the user reading the displayed eye chart at the visual acuity testing distance; and receive a user input indicating that the user has completed reading the displayed eye chart.

14. The computer-readable medium of claim 13, further comprising instructions that cause the processing unit to:

instruct the user to move towards the user device if the determined current distance is greater than the visual acuity testing distance; and instruct the user to move away from the user device if the current determined distance is less than the visual acuity testing distance.

15. The computer-readable medium of claim 13, wherein the predetermined interpupillary distance is an interpupillary distance that is representative of a population of people other than the user.

16. The computer-readable medium of claim 13, wherein the predetermined interpupillary distance is a value that represents a median interpupillary distance among the population.

17. The computer-readable medium of claim 13, further comprising instructions that cause the processing unit to select the predetermined interpupillary distance from a set of interpupillary distances.

18. The computer-readable medium of claim 17, further comprising instructions that cause the processing unit to select the predetermined interpupillary distance from the set of interpupillary distances based on the sex of the user.

19. The computer-readable medium of claim 17, further comprising instructions that cause the processing unit to select the predetermined interpupillary distance from the set of interpupillary distances based on the age of the user.

20. The computer-readable medium of claim 13, further comprising instructions that cause the processing unit to:

transmit the video to the remote eye test system via the network; and receive a prescription from the remote eye test system in response to the transmitted video.

21. The computer-readable medium of claim 13, wherein the camera is included on the user device.

22. The computer-readable medium of claim 13, further comprising instructions that cause the processing unit to generate random characters for the eye chart.

* * * * *